US005668265A

United States Patent [19]
Nadeau et al.

[11] Patent Number: 5,668,265
[45] Date of Patent: Sep. 16, 1997

[54] BI-DIRECTIONAL OLIGONUCLEOTIDES THAT BIND THROMBIN

[75] Inventors: James G. Nadeau, Chapel Hill, N.C.; Mary Lee Ciolkowski, Portage, Mich.; Erwin A. Vogler, Newhill, N.C.

[73] Assignee: Becton Dickinson and Company, Franklin Lakes, N.J.

[21] Appl. No.: 614,447

[22] Filed: Mar. 12, 1996

Related U.S. Application Data

[63] Continuation of Ser. No. 252,071, May 31, 1994, abandoned.

[51] Int. Cl.$^6$ .............................. C07H 21/04; C12Q 1/68; A61K 35/00
[52] U.S. Cl. .............................. 536/23.1; 435/6
[58] Field of Search .............................. 536/23.1; 435/6; 514/44

[56] References Cited

U.S. PATENT DOCUMENTS 5,399,676  3/1995  Froehler .............................. 536/23.1

OTHER PUBLICATIONS

Bock et al (1992) "Selection of single-stranded DNA molecules that bind and inhibit human thrombin" Nature 355:564–566.

Griffin et al (1993) "The discovery and characterization of a novel nucleotide-based thrombin inhibitor" Gene 137:25–31.

Echer et al. (1993) "Rational screening of oligonucleotide combinational libraries for drug discovery" Nucleic Acids Research 21:1853–1856.

Shaw et al (1991) "Modified oligonucleotides stable to exonuclease degradation in serum." Nucleic Acids Res. 19:747–750.

Huizenga et al (1995) "A DNA aptamer that binds adenosine and ATP" Biochem. 34:656–665.

Giver et al. (1993) "Selection and design of high-affinity RNA ligands for HIV-1 Rev." Gene 137:19–24.

Latham et al (1994) "The application of a modified nucleotide in aptamer selection: etc." Nucleic Acids Res. 22:2817–2822.

Lorsch et al (1994) "In vitro selection of RNA aptamers specific for Cyanocobalamin" Biochemistry 33:973–982.

*Primary Examiner*—Jasemine C. Chambers
*Assistant Examiner*—Scott D. Priebe
*Attorney, Agent, or Firm*—David W. Highet, Esq.

[57] ABSTRACT

The present invention relates to bi-directional nucleic acid ligand compounds wherein at least two oligonucleotides of opposite sequence polarity are linked to a connecting compound at their same respective terminii; either the 5' terminii or the 3' terminii. These compounds are useful for binding protein or small molecule targets and thus may be used as diagnostic or therapeutic agents.

17 Claims, 3 Drawing Sheets

SYNTHETIC CONNECTING CHAIN

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 7 base pairs
        ( B ) TYPE: nucleic acid
        ( C ) STRANDEDNESS: single ( D ) TOPOLOGY: linear ( i i ) MOLECULE TYPE: DNA (genomic)

( x i ) SEQUENCE DESCRIPTION: SEQ ID NO:1:

GGTTGGT                                                                                             7

( 2 ) INFORMATION FOR SEQ ID NO:2:

( i ) SEQUENCE CHARACTERISTICS:
                ( A ) LENGTH: 8 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:2:

GGTTGGTT                                                                                            8

( 2 ) INFORMATION FOR SEQ ID NO:3:

( i ) SEQUENCE CHARACTERISTICS:
                ( A ) LENGTH: 9 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:3:

GGTTGGTTG                                                                                           9

( 2 ) INFORMATION FOR SEQ ID NO:4:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:4:

GGTTGGTGTG GTTGG                                                                                    15

BI-DIRECTIONAL OLIGONUCLEOTIDES THAT BIND THROMBIN

This application is a continuation of application Ser. No. 08/252,071, filed May 31, 1994, now abandoned.

FIELD OF THE INVENTION

The present invention broadly relates to a new class of nucleic acid ligand compounds in which at least two oligonucleotides of opposite sequence polarity act in concert to form a binding site for a protein.

BACKGROUND OF THE INVENTION

Nucleic acid ligands which bind protein are known to those skilled in the art through Patent Cooperation Treaty International Publication No. WO91/19813 which was published on Dec. 26, 1991, the related U.S. Pat. No. 5,270,163, and other publications with related disclosures such as Tuerk, C. and Gold, L., *Science* 249, 505–510 (1990), Irvine, D. et al., *J. Mol. Biol.* 222, 739–761 (1991), and Tuerk, C. et al., *Proc. Natl. Acad. Sci. USA* 89, 6988–6992 (1992). Nucleic acid ligands are defined as nucleic acid molecules, each having a unique sequence, each of which has the property of binding specifically to a desired target compound or molecule. The nucleic acid ligands have sufficient capacity for forming a variety of two- and three-dimensional structures and sufficient chemical versatility available within their monomers to act as ligands (form specific binding pairs) with virtually any chemical compound, whether monomeric or polymeric. The nucleic acid ligands may be made up of double or single stranded RNA or DNA and there may be more than one ligand for a given target. However, the ligands generally differ from one another in their binding affinities for the target molecule.

The nucleic acid ligands have structures or motifs that have been shown to be most commonly involved in non-Watson-Crick type interactions. Included among these structures or motifs are hairpin loops, symmetric and asymmetric bulges, pseudoknots, guanosine quadraplexes (or G-tetrads) and combinations thereof.

Also known in the art are reverse polarity sequences. For example, parallel stranded DNA has been synthesized in the form of hairpins with four-nucleotide central loops (consisting of either C or G) as described by van de Sande, J. H. et al., *Science* 241, 551 (1988). Also, the third oligodeoxyribonucleotide used in triple helix formation has its polarity reversed at about its midpoint as described by Horne, D. A. and Dervan, P. B., *J. Am. Chem. Soc.* 112, 2435 (1990) and PCT International Publication No. WO 91/06626. Furthermore, an oligonucleotide produced by the inversion of its 3' terminal linkage to yield a 3'—3' linkage and two 5' ends has shown increased stability to degradation in cell culture and serum. Shaw, J. et al., *Nuc. Acids Res.* 19, 747 (1991).

SUMMARY OF THE INVENTION

The bi-directional nucleic acid ligand compounds of the present invention represent a new class of compounds wherein at least two oligonucleotides of opposite sequence polarity are linked to a connecting compound at their same respective terminii. When the oligonucleotides are linked at their respective 3' terminii, the compounds do not contain a 3' terminal nucleoside, and therefore are resistant to 3' exonucleases. Furthermore, such reverse sequence motifs expand the number of options available to researchers attempting to identify nucleic acid ligand compounds with specific binding properties.

BRIEF DESCRIPTION OF THE DRAWING

The various objects, advantages and novel features of the invention will be more readily appreciated from the following detailed description when read in conjunction with the appended figures, in which.

DETAILED DESCRIPTION OF THE INVENTION

Figure 1A:
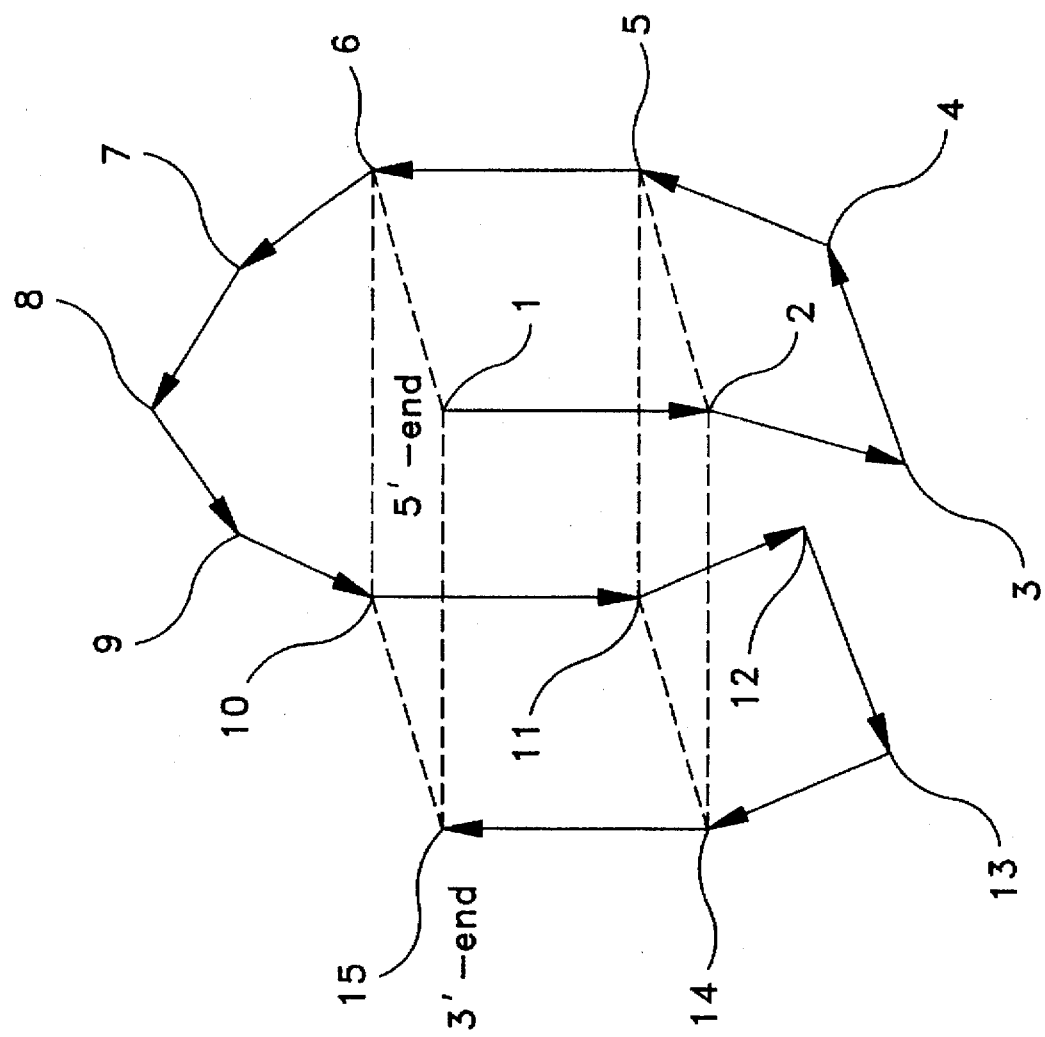
FIG. 1A and 1B are schematic representations of the three-dimensional configuration of a previously known oligonucleotide which binds thrombin (1A) and the probable three-dimensional structure of a bi-directional nucleic acid ligand compound which binds thrombin (1B)

As stated above, the present invention relates to a bi-directional nucleic acid ligand compound wherein at least two oligonucleotides of opposite sequence polarity are linked at their respective 3' terminii to a connecting compound or linked at their respective 5' terminii to a connecting compound. These nucleic acid ligand compounds are useful to bind proteins or proteinaceous materials, and thus may be utilized as diagnostics to determine the presence or absence of a target compound which is indicative of a disease. Similarly these nucleic acid ligand compounds may be used as therapeutic agents which bind to a disease causitive agent to inactivate or remove that agent.

The oligonucleotides of opposite sequence polarity are selected based on the identification of unidirectional nucleic acid ligands which bind a desired target compound. From this knowledge, bi-directional oligonucleotides can be synthesized which have similar three-dimensional molecular structures. Alternatively, bi- or multi-directional nucleic acid ligands can be selected directly from a random pool of bi- or multi-directional oligonucleotides. It is generally accepted that the particular three-dimensional structure of a nucleic acid ligand molecule determines that molecule's binding specificity and affinity for a particular target molecule.

The bi-directional nucleic acid ligand compounds of the present invention can also be constructed by linking two or more complete nucleic acid ligands with affinity for the same target to a connecting compound through their same respective terminii. These bi-directional nucleic acid ligand compounds can potentially bind at more than one binding site on the target and thus have higher binding affinity for target than either nucleic acid ligand alone. In addition, when these nucleic acid ligands are linked to the connecting compound through their respective 3' terminii, the resultant bi-directional nucleic acid ligand compound will be resistant to degradation by 3' exonucleases.

Oftentimes, all that is required is the reversal of sequence polarity at the 3' end of a nucleic acid ligand that has been found to bind a target. For example, a known nucleic acid ligand which binds thrombin has the sequence 5'-GGTTGGTGTGGTTGG-3' (SEQ ID NO:4) (see Bock, L. C. et al., *Nature* 355, 564 (1992)). Therefore, from this sequence, a seven nucleotide sequence, 5'-GGTTGGT-3' (SEQ ID NO:1) was selected as the oligonucleotide to be linked to a connecting compound to form a nucleic acid ligand compound of the present invention which binds thrombin.

In order to identify unidirectional nucleic acid ligands upon which to base the bi-directional oligonucleotides of the present invention, nucleic acid ligands which bind the desired target must first be identified, and then the three-dimensional structures of these ligands must be determined. Numerous nucleic acid ligands which bind desired target protein molecules have been identified. For example RNA nucleic acid ligands have been identified that have high affinity and specificity for: (1) bacteriophage T4 DNA polymerase (Tuerk, C. and Gold, L., *Science* 249, 505 (1990)); (2) R17 coat protein (Schneider, D. et al., *J. Mol. Biol.* 228, 862 (1992)); (3) human immunodeficiency virus (HIV) reverse transcriptase (Tuerk, C. et al. *Proc. Nat'l. Acad. Sci. USA* 89, 6988 (1992)); (4) HIV rev protein (Bartel, D. P. et al., *Cell.* 67, 529 (1991)); (5) basic fibroblast growth factor (Jellineck, D. et al., *Proc. Nat'l. Acad. Sci. USA* 90, 11227 (1993)); (6) adenosine triphosphate (Sassanfar, M. and Szostak, J. W., *Nature* 364, 550 (1993)); and (7) theophylline (Jenison, R. D. et al., *Science* 263, 1425 (1994)); and (8) several amino acids (Farmulok, M. and Szostak, J. W., *J. Am. Chem. Soc.*, 114, 3990 (1992) and Connell, G. J. et al., *Biochemistry* 32, 5497 (1993)). Similarly, DNA and RNA nucleic acid ligands that bind to organic dyes have also been identified (Ellington, A. and Szostak, J., *Nature* 346, 618 (1990) and Ellington, A. and Szostak, J., *Nature* 355, 850 (1992)). Furthermore, nucleic acid ligands that bind other protein and small molecule targets will continue to be identified by use of the SELEX method taught in such publications as PCT International Publication No. WO 91/19813 and U.S. Pat. No. 5,270,163.

A method for identification of nucleic acid ligands that bind protein and small molecule targets is the oligonucleotide combinatorial technique described by Ecker, D. J. et al., *Nuc. Acids Res.* 21,1853 (1993). This method is known as synthetic unrandomization of randomized fragments (SURF). The SURF method takes advantage of the shapes recognized by Tuerk, C. and Gold, L. (*Science* 249, 505 (1990), and is based on repetitive synthesis and screening of increasingly simplified sets of oligonucleotide analogue pools. The starting pools consist of oligonucleotide analogues of defined length with one position in each pool containing a known analogue and the remaining positions containing equimolar mixtures of all other analogues. With each additional step of the method, at least one additional position of the oligomer is determined until the nucleic acid ligand is uniquely identified. In principle a similar approach can be used to select bi- or multi-directional nucleic acid ligands from a random pool of bi- or multi-directional oligonucleotides constructed by using mixtures of 5' and 3' phosphoramidites during synthesis of the oligonucleotide pool.

Once a particular nucleic acid ligand has been identified through the SELEX process or other selection process, its nucleotide sequence can be determined using sequencing gels or commercially available sequencers or other techniques known to those skilled in the art. Also, its three-dimensional molecular structure can be determined by nuclear magnetic resonance (NMR), particularly $^1$H NMR spectra. The imino proton spectra of nucleic acids yield qualitative information on secondary structure and can be used to monitor base pair formation as taught by van de Ven, F. J. M. and Hilbers, C. W., *Eur. J. Biochem.* 178, 1 (1988); Clore, G. M. and Gronenborn, A. M., *CRC Crit. Rev. Biochem. Mol. Biol.* 24, 479 (1989); and Wuthrich, K. *NMR of Proteins and Nucleic Acids*, Wiley, New York (1986). The NMR spectra are generally obtained using spectrometers such as the Varian XL-400, VXR-400, and the Bruker AM-600. The orientation and position of target molecules for nucleic acid ligands can be determined by molecular placement using programs such as X-PLOR (Brunger, A. T. (1992) *X-PLOR Manual*, Version 3.0, Yale University, New Haven, Conn.). These determinations may then be refined using programs such as PROFFT (Finzel, B. C. (1987) *J. Appl. Crystallogr.* 20, 53–55). These same programs may then be used to determine and refine the binding relationship between the target molecule and the nucleic acid ligand. These techniques are fully explained in relation to the determination of the three-dimensional structure of a nucleic acid ligand that binds thrombin in Padmanabhan, K. et al., *J. Biol. Chem.* 24, 17651 (1993); Wang, K. Y. et al., *Biochemistry* 32, 1899 (1993); and Macaya, R. F. et al., *Proc. Nat'l. Acad. Sci. USA* 90, 3745 (1993).

For optimal performance as part of the nucleic acid ligand compounds of the present invention the oligonucleotides should be at least 5 bases in length, and preferably between 5 bases and 15 bases in length. Also, the oligonucleotide residues used in the present invention may be either deoxyribonucleotides, ribonucleotides or ribonucleotide derivatives. One particularly useful oligonucleotide for use as part of a nucleic acid ligand compound to bind to the enzyme, thrombin is the sequence 5'-GGTTGGT-3' (SEQ ID NO:1). Another useful sequence is 5'-GGTTGGTT-3' (SEQ ID NO:2). At least two copies of an oligonucleotide of a desired sequence are linked to a connecting compound at their respective 3' terminii to form nucleic acid ligand compounds of the present invention which bind thrombin. Furthermore, in some instances the sequence on one side of the connecting compound can be different than the sequence on other side. For example, it was found that a nucleic acid ligand compound which binds thrombin could be produced by linking an oligonucleotide of SEQ ID NO:2 through its 3' terminus to a connecting compound and linking a second oligonucleotide of sequence 5'-GGTTGGTTG-3' (SEQ ID NO:3) (i.e. one additional base, G, to SEQ ID NO:2) through its 3' terminus to the connecting compound.

A principal advantage of linking the oligonucleotides to the connecting compound through their 3' terminii is the resultant stability of the nucleic acid ligand compound, particularly in biological samples such as serum. Serum is known to contain 3' exonucleases. However, at least one embodiment of the nucleic acid ligand compounds of the present invention is resistant to degradation by 3' exonucleases because their 3' ends are not exposed, but instead are linked to the connecting compound.

In the current embodiments, the size of the connecting compounds linking the bi-directional oligonucleotide segments ranges from two rotatable covalent bonds contained in a single phosphodiester linkage (compounds 1–4 in Example 3) to 22 rotatable bonds contained in the hexaethylene glycol-phosphodiester linkages of compounds 5–7, Example 3. One function of the linker is to facilitate interaction between the two bi-directional segments by holding them in close proximity while still allowing adequate separation and flexibility to permit the essential interactions to occur. When short connecting compounds are used (such as a single phosphodiester linkage), the lack of sufficient separation and flexibility may be overcome by adding "spacer" nucleotides to the bi-directional oligonucleotide segments. (In the case of the thrombin-binding bi-directional nucleic acid ligand compounds, spacer nucleotides are defined as nucleotides between the GGTTGG segments). As a result of findings in the current invention, the spacer nucleotides are not thought to be directly involved in the essential interactions between regions of opposite sequence polarity, but instead play an indirect role by providing essential spacing and flexibility to allow these interactions (between GGTTGG segments) to occur freely. For example, in the case where a single phosphodiester group joins bi-directional segments, a total of at least 5 spacer nucleotides is required between the two bi-directional GGTTGG segments to give optimal thrombin binding (see compound 4, Example 3), presumably by permitting these segments to fold into a G-tetrad-containing structure thought to be essential for thrombin binding (see discussion below). When connecting compounds longer than a single phosphodiester linkage are used, correspondingly fewer spacer nucleotides are needed to produce optimal thrombin binding. For example, when hexaethylene glycol is the connecting compound, only two spacers (and possibly fewer) are needed to give thrombin binding comparable to 5 spacer nucleotides when the connecting compound is a single phosphodiester group (compare compounds 3 and 5 in Example 3). The optimal number of spacer nucleotides may depend on whether the bi-directional nucleic acid ligand compounds are 3'—3' or 5'—5' linked (compare compounds 2 and 4 in Example 3).

The precise chemical composition of the connecting compounds is not expected to be a critical factor provided the connecting compound possesses the needed length and flexibility. Very long connecting compounds (>30 rotatable covalent bonds) or many (>10) spacer nucleotides are expected to result in reduced thrombin binding affinity due to diminished propinquity of the GGTTGG segments or other bi-directional segments, though in general optimal connecting compound length will depend on the structural features of the bi-directional nucleic acid ligand compound in question. In the current embodiments, phosphodiester linkages are used to join the oligonucleotide segments either to each other or to a common linking compound. Other means of making these connections are also possible. These include but are not limited to moieties of the formula P(O)S, P(S)S, P(O)NR$_2$, P(O)R, P(O)OR, CO, CONR$_2$ (R=1–6 carbon alkyl group)joined to adjacent nucleotides or linkers through —O— or —S—. Furthermore, in the current embodiments, all internucleotide linkages are phosphodiester bonds, which may also be replaced, in part or in total, by the aforementioned linkages. In addition, the nucleotide residues of the current embodiments may be replaced, in part or in total, by residues known as peptide nucleic acids (Nielsen, P. E., et al, *Bioconjugate Chem.* 5, 3, (1994)).

Thus, a suitable bi-directional nucleic acid ligand compound to bind thrombin contains two copies of SEQ ID NO:1 bound at their 3' ends through phosphodiester linkages to hexaethylene glycol to form a molecule with bi-directional sequence polarity. This compound binds thrombin with high affinity ($K_a > 10^7 M^{-1}$). This affinity is comparable to that of the known nucleic acid ligand 5'-GGTTGGTGTGGTTGG-3' (SEQ ID NO:4) which also binds thrombin.

Furthermore, both copies of SEQ ID NO:1 are required for the high thrombin affinity, because a single copy of this sequence does not have high affinity for thrombin. The two copies or segments of opposite sequence polarity act in concert to form a binding site for thrombin.

Another suitable bi-directional nucleic acid ligand compound to bind thrombin contains two copies of the sequence 5'-GGTTGGTT-3' (SEQ ID NO:2) bound at their 3' ends through phosphodiester linkages to hexaethylene glycol. This compound also exhibits high affinity for thrombin and inhibits thrombin in porcine plasma as explained in greater detail in the Examples.

Figure 1B:
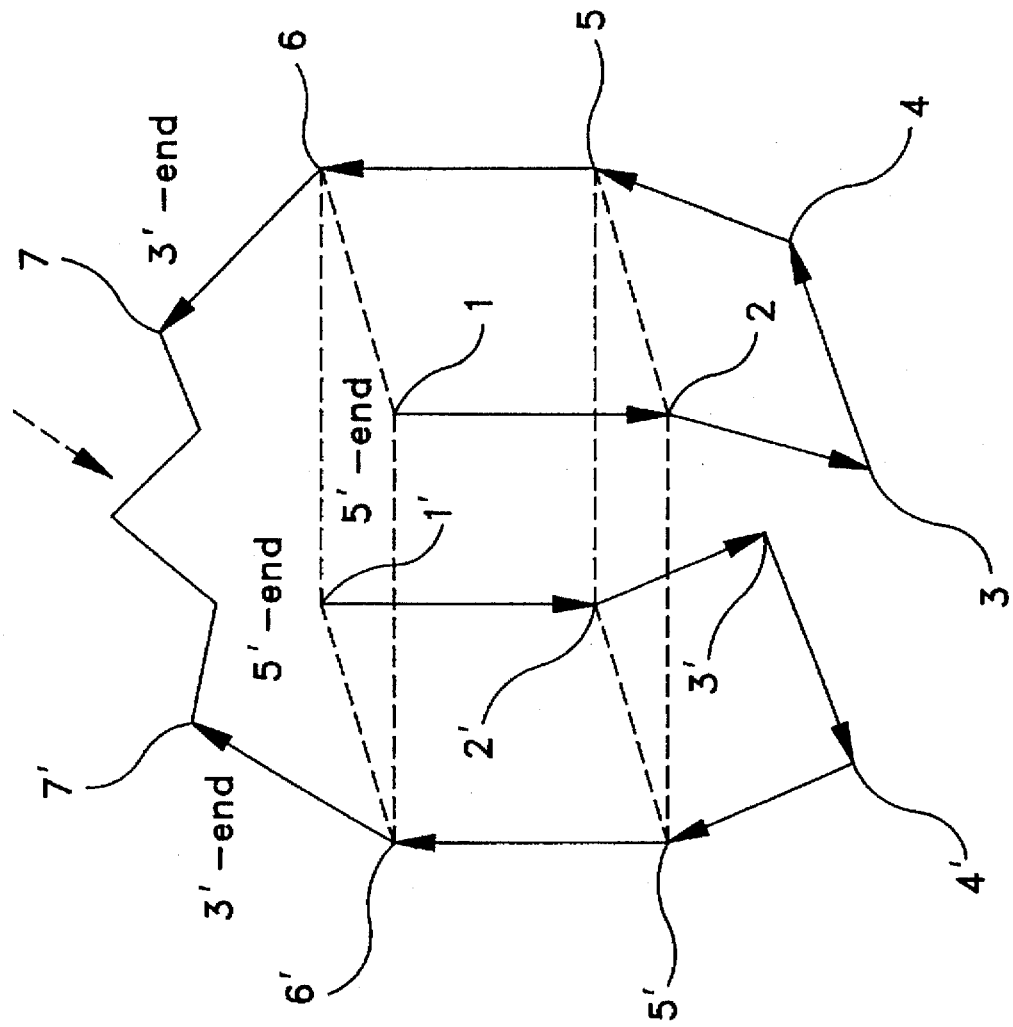

Because of their bi-directional nature, the nucleic acid ligands of the current invention cannot fold into the same 3-dimensional structure adopted by the unidirectional nucleic acid ligand known to bind thrombin (see FIG. 1 and discussion below). Furthermore, in view of conventional wisdom in the art and the structural differences outlined below, the bi-directional nucleic acid ligands were not expected to bind thrombin with affinities comparable to the unidirectional nucleic acid ligand. Thus, the high thrombin affinity of the bi-directional nucleic acid ligand compounds of the current invention was surprising.

The structure of the unidirectional consensus nucleic acid ligand that binds thrombin was recently determined by means of NMR spectroscopy (Macaya, R. F. et al., *Proc. Nat'l. Acad. Sci. USA* 90, 3745 (1993); Wang, K. Y. et al, *Biochemistry* 32, 1899 (1993)). This molecule folds into a compact structure consisting of (i) two G-tetrads stacked together, (ii) two TT loops that span the narrow groove of the bottom G-tetrad, and (iii) a TGT loop that spans the wide groove of the upper G-tetrad. Each TT and TGT loop runs along an edge of the square formed by the G-tetrad, resulting in a chair-like structure depicted in FIG. 1. Recently, the structure of the complex formed between thrombin and this uni-directional consensus nucleic acid ligand was determined by x-ray crystallography (Padmanabhan, K. et al. *J. Biol. Chem.* 268, 17651 (1993)). This structure shows the upper (i.e., the TGT) loop of the nucleic acid ligand bound to the fibrinogen exosite of thrombin. Ionic interactions between lysine residues of the protein and the phosphate oxygens of the upper (TGT) loop seem to be key interactions for binding of the nucleic acid ligand to the fibrinogen exosite of thrombin. Thus, one expects that the presence and appropriate positioning of key phosphate groups in this upper loop should be essential to high affinity binding of the nucleic acid ligand to the fibrinogen exosite of thrombin. The crystal structure of the complex also reveals that the putative heparin binding site on a second molecule of thrombin can bind to the lower (i.e. TT) loops of the nucleic acid ligand, forming a sandwich-like structure with the nucleic acid ligand in the middle bound through its upper TGT loop to the fibrinogen exosite of one thrombin molecule and through its lower TT loops to the putative heparin exosite of a second thrombin molecule. From the crystal structure, it is not clear which, if either, of these binding modes predominates under solution-phase conditions. However, recent competitive-binding and chemical modification studies (Paborsky, L. R., et al., *J. Biol. Chem.* 268, 20806 (1993)), indicate that, in solution, the consensus nucleic acid ligand binds to the fibrinogen exosite of thrombin and in so doing prevents thrombin from binding to and cleaving fibrinogen. This competitive inhibition is believed to be responsible for the anticoagulative activity of the nucleic acid ligand.

The crystallographic x-ray structure of the thrombin-nucleic acid ligand complex taken in combination with the solution phase binding studies lead to the expectation that the upper loop of the nucleic acid ligand plays a key role in the binding and inhibition of thrombin in solution. This expectation is supported by the fact that replacement of either nucleotide $G_8$ or $T_9$ (numbered from the 5' end) (both shown by x-ray crystallography to border a key phosphate group involved in thrombin binding) with an abasic residue results in sharply diminished ability of the nucleic acid ligand to inhibit thrombin (PCT International Publication No. WO 92/14842). Consequently, one expects that significant modifications of the upper (TGT) loop will result in much reduced thrombin binding.

The structures of the bi-directional nucleic acid ligand compound of the present invention are unknown but may be determined by methods employed in the structural derivation of the unidirectional consensus nucleic acid ligand compound (Macaya et al., supra; Wang et al., supra). It is expected that the bi-directional molecules will fold into structures containing two G-tetrads and two TT loops, much as observed in the unidirectional nucleic acid ligand compound (see FIG. 1). In contrast to the consensus nucleic acid ligand, however, the upper loop of the bi-directional molecules (comprised of the synthetic connecting chain) cannot bridge the edge of the upper G-tetrad but must instead span the diagonal of the tetrad. The energetic feasibility of such diagonal-spanning structures has been confirmed by molecular modeling of a bi-directional nucleic acid ligand compound containing glycerol as the connecting chain. The change in the upper loop position of these structures, relative to the unidirectional nucleic acid ligand, is a direct consequence of the bi-directional nature of the nucleic acid ligand compound of the present invention. Because the upper loop of the unidirectional nucleic acid ligand was previously identified as the structural element of the nucleic acid ligand that binds to the fibrinogen exosite of thrombin (see discussion above), the repositioning of this loop in the bi-directional nucleic acid ligand compounds would be expected to substantially alter the ability of these molecules to bind thrombin. Unexpectedly, however, the bi-directional nucleic acid ligand compound exhibit binding affinities comparable to the unidirectional consensus nucleic acid ligand.

High thrombin affinity is exhibited by the bi-directional nucleic acid ligand compounds of the present invention containing any one of three types of connecting groups to join the bi-directional GGTTGG segments. Thus the precise chemical composition of the connecting compound does not appear to be of critical importance, provided the connecting compound contains the necessary length and flexibility to allow G-tetrad formation between the two GGTTGG segments. This suggests that the GGTTGG segments, and not the upper connecting loop, are the segments of the nucleic acid ligand involved in binding to the fibrinogen exosite. For optimal thrombin binding, the bi-directional nucleic acid ligand compounds must contain either (i) 5 (or more) spacer nucleotides between the two inverted GGTTGG segments or (ii) fewer nucleotides and a longer connecting chain such as glycerol or hexaethylene glycol. Thus, the optimal spacer length between GGTTGG segments in bi-directional nucleic acid ligand compounds is longer than the 3 nucleotide spacer (TGT) found to be optimal for the unidirectional nucleic acid ligand (Block et al. *Nature* 355, 564 (1992)). This difference may be at least partly due to the greater distance that must be covered by a loop spanning the diagonal, rather than the edge, of the upper G-tetrad.

All bi-directional nucleic acid ligand compounds that bind thrombin and are disclosed in the present document contain at least one T nucleotide flanking each 5'GGTTGG3' segment, such that the flanking T nucleotide(s) are positioned between the GGTTGG sequences and the connecting compound. It is conceivable that two 5'GGTTGG3' attached directly to the connecting compound (L) in a bi-directional manner (e.g., $^{5'}$GGTTGG$^{3'}$-L-$^{3'}$-GGTTGG$^{5'}$) would also exhibit high thrombin affinity. In support of this contention is the observation, first disclosed here, that the unidirectional nucleic acid ligand $^{5'}$-GGTTGG$^{3'}$ pL$_1$p $^{5'}$GGTTGC$^{3'}$ (where pL$_1$p represents hexaethylene glycol connected by phosphodiester linkages to the oligonucleotide segments) does in fact bind to thrombin with high affinity, though about 5-fold weaker than the consensus nucleic acid ligand (see Example 3). Thus, at least in the uni-directional nucleic acid ligand, spacer nucleotides are not required for high affinity binding, although their presence does improve this affinity by about 5-fold. Similar results are expected for bi-directional nucleic acid ligand compounds of the present invention.

The findings of the present invention that various compositions can serve as suitable linkers for the thrombin nucleic acid ligand also suggests that various nucleic acid structural components may be incorporated into the upper loop of the nucleic acid ligand. For example, a nucleotide sequence such as $^{5'}$GGTTGG-a-XYZ-b-Z'Y'X'-c-GGTTGG$^{3'}$ (where a, b and c are arbitrary linking compounds and may be nucleotides or other material such as but not limited to glycerol or hexaethylene glycol; and where XYZ represents a nucleotide sequence that has Watson-Crick complementarity to sequence Z'Y'X') would be expected to fold into a chair-like structure as in FIG. 1A, except that the upper loop would also contain a hairpin structure resulting from the Watson-Crick base-pairing of XYZ and Z'Y'X'. Such an additional structural feature would be expected to add stability to the chair-like conformation and consequently increase thrombin affinity. Similar structural features could also be incorporated into bi-directional nucleic acid ligand compounds.

In addition, the present findings that connecting compounds are not of critical importance to thrombin binding also raises the possibility that GGTTGG segments may be brought into suitable proximity (to facilitate G-tetrad formation) by means other than covalent attachment (of the GGTTGG segments) to a common connecting compound. For example, the two oligonucleotides $^{5'}$XYZ-a-GGTTGC$^{3'}$ and $^{5'}$GGTTGG-b-Z'Y'X'$^{3'}$ (where a, b, XYZ and Z'Y'X' are as defined above) would be expected to bind to each other in solution both through Watson-Crick pairing of the XYZ/Z'Y'X' segment and through G-tetrad formations of the GGTTGG segments (as in FIG. 1) to form a bi-directional molecular nucleic acid ligand able to bind thrombin with high affinity. Fluorescent resonance energy transfer (see for example, Sixou, S., et al. *Nucleic Acids Res.* 22, 622 (1994)) may be used in conjunction with such bi-molecular nucleic acid ligands to allow homogenous detection of thrombin binding, or other binding events of other target-nucleic acid ligand combinations.

The binding of thrombin (or other target molecule) to a nucleic acid ligand can, in principle, be modulated by addition of a second oligonucleotide molecule possessing partial or total Watson-Crick complementarity to the nucleic acid ligand. This second oligonucleotide will compete against thrombin (or other target) for the opportunity to bind to the nucleic acid ligand. Thus, an oligonucleotide complementary to the nucleic acid ligand could be used to reverse the binding of thrombin (or other target) to the nucleic acid ligand. In the case of bi-directional nucleic acid ligand compounds, the complementary oligonucleotides will in general also need to be bi-directional in order to maintain the standard (i.e., anti-parallel) Watson-Crick complementarity across regions of inverted sequence polarity. For example, the oligonucleotide with Watson-Crick complementary to the bi-directional nucleic acid ligand compound $^{5'}$GGTTGGTTG$^{3'}$TTGGTTGG$^{5'}$ will be $^{3'}$CCAACCAAC$^{5'}$Y$^{5'}$AACCAACC$^{3'}$, where X and Y are linking compounds (such as a phosphodiester group, glycerol, hexaethylene glycol, etc.) and X may or may not be identical to Y. If the nucleic acid ligand contains a 3'—3' linkage, then the complementary sequence will contain a 5'—5' linkage, and vice versa.

The target compounds that may be detected utilizing the bi-directional nucleic acid ligand compounds of the present invention include any compound of interest. For example a target compound can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, enzyme, etc., without limitation. As will be recognized by those skilled in the art, the target compounds that may be detected include certain compounds which are not detectable utilizing conventional antibody based biosensors, for example, glucose, cyclic AMP, and catecholamines, in general, molecules for which antibodies are difficult or impossible to obtain.

Since one use of the nucleic acid ligand components is for detection of target compounds for the clinical diagnosis of physiologic conditions, the nucleic acid ligand compounds will most frequently be contacted with biological material which may or may not contain the target compound of interest. Such biological materials include blood, plasma, serum, sputum, urine, semen, cerebrospinal fluid, bronchial aspirate, and macerated tissue. Other samples which m, ay be brought into contact with the nucleic acid ligand compounds of the present invention include foods and environmental discharges such as liquid wastes. The in vivo monitoring stability of nucleic acid ligands enables one to test in unique environments.

The detection of the presence of the target compound bound to the nucleic acid ligand compound may be measured by any suitable means such as fluorescence, chemiluminescence, surface plasmon resonance, and/or related optical techniques such as ellipsometry. Such detection techniques are well known to those skilled in the art.

The invention is further described by the following examples which are offered by way of illustration and are not intended to limit the invention in any manner. In these examples, all percentages are by weight if for solids and by volume if for liquids, and all temperatures are in degrees Celsius unless otherwise noted.

EXAMPLE I

Preparation of Bi-directional Nucleic Acid Ligand Compounds with a Phosphodiester Linkage Oligonucleotides containing segments of reverse sequence polarity connected through a single phosphodiester linkage were prepared essentially as described by van de Sande, J. H. et al. *Science* 241, 551 (1988). The compounds were prepared by solid-phase synthesis on an Applied Biosystems DNA synthesizer using standard phosphoramidite coupling chemistry with some special reagents as described below.

To prepare oligonucleotides containing 3'—3' internucleotide linkages, synthesis was first performed in the 5'→3' direction beginning with 5'-derivatized CpG columns (dG-5'-1caa CpG, 1 µmole, Glen Research) and 5'-phosphoramidites (dT-5'-CE phosphoramidite and dG-5'-CE phosphoramidite from Glen Research). Subsequent coupling cycles were repeated in the 5'→3' direction until the first of the two bi-directional segments was complete. The direction of synthesis was reversed from 5'→3' to 3'→5', by simply replacing 5'-phosphoramidites with standard 3'-phosphoramidites (ABI). The first linkage formed after the reversal of synthesis direction was a 3'—3' internucleotide linkage. Subsequent couplings were repeated in the 3'→5' direction (forming 3'5' linkages) until the second of the two bi-directional segments was complete.

An analogous procedure was followed for preparation of 5'—5' linked oligonucleotides (i.e. van de Sande, J. H. et al., *Science* 241, 551 (1988)). However, in this case, synthesis was begun in the 3'→5' direction from a 3-derivatized CpG column (ABI), using standard 3'-phosphoramidites (ABI).

After completion of the first segment, the direction of synthesis was reversed (to 5'→3') by switching from 3'- to 5-phosphoramidites, resulting in the formation of a 5'—5' internucleotide linkage, followed by 5'—3' internucleotide bond formation until the desired sequence was achieved.

After the syntheses and following detritylation, the oligonucleotides were released from the CpG columns and deprotected by treatment with concentrated ammonia (12–14 hours, 56° C.). The oligomers were then purified by denaturing gel electrophoresis, followed by ethanol precipitation.

The following compounds were prepared by this method:

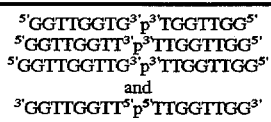

where p represents a phosphodiester linkage=— O—PO(O)—O— where the underlined oxygens belong to the 5' or 3' position of the pentose moieties of the flanking nucleotides.

These same techniques can be used to construct bi-directional nucleic acid ligand compounds with a phosphodiester linkage wherein the oligonucleotide segments of opposite sequence polarity are portions of nucleic acid ligands known to have affinity and specificity for certain targets such as (1) bacteriophage T4 DNA polymerase (Tuerk, C. and Gold, L., *Science* 249, 505 (1990)); (2) R17 coat protein (Schneider, D. et al., *J. Mol. Biol.* 228, 862 (1992)); (3) human immunodeficiency virus (HIV) reverse transcriptase (Tuerk, C. et al., *Proc. Nat'l. Acad. Sci. USA* 89, 6988 (1992)); (4) HIV rev protein (Bartel, D. P. et al., *Cell.* 67, 529 (1991)); (5) basic fibroblast growth factor (Jellineck, D. et al., *Proc. Nat'l. Acad. Sci. USA* 90, 11227 (1993)); (6) adenosine triphosphate (Sassanfar, M. and Szostak, J. W., *Nature* 364, 550 (1993)); and (7) theophylline (Jenison, R. D. et al., *Science* 263, 1425 (1994)). Similarly, the same techniques can be used to construct bi-directional nucleic acid ligand compounds wherein the oligonucleotide segments of opposite sequence polarity are different nucleic acid ligands that have affinity and specificity for the same target. Such nucleic acid ligands can be identified from the same or different rounds of a SELEX process.

EXAMPLE 2

Preparation of Bi-directional Nucleic Acid Ligand Compounds with Glycerol Phosphodiester Linkages and Hexaethylene Glycol Phosphodiester Linkages This example describes preparation of nucleic acid ligand compounds in which the segments of opposite sequence polarity are connected indirectly by linkage to a common neutral compound, which in this Example is either glycerol or a hexaethylene glycol chain.

A. Bi-directional oligonucleotide linkage through a hexaethylene glycol.

Each of the two oligonucleotide segments in the molecule can be connected to the linker either through their 5' or 3' ends. For attachment to through the 3' ends, the first of the two segments was synthesized in the 5'→3' direction as described in Example 1. After this segment was complete, its 3' end was coupled, by standard phosphoramidite chemistry on an ABI synthesizer, to the Spacer Phosphoramidite (Clonetech), which is a tritylated and phosphoramidite-containing derivative of hexaethylene glycol. Synthesis of the second of the two bi-directional segments was then begun, in the 3'→5' direction, by coupling of a 3'-phosphoramidite to the detritylated end of the hexaethylene glycol moiety. Synthesis continued in the 3'→5' direction until the second oligonucleotide segment was complete. The resulting compound thus consisted of two oligonucleotide sequences of reverse sequence polarity linked through their 3' ends to opposite ends of hexaethylene glycol phosphodiester.

An analogous procedure is followed for preparation of bi-directional oligonucleotides joined by attachment of their 5' ends to a common hexaethylene glycol phosphodiester linker. In this case, synthesis was begun in the 3'→5' direction, using a 3'-derivatized CpG column (1 μmole, ABI) and 3'-phosphoramidites (ABI). After synthesis of the first segment was complete, the 5' end of the nascent compound was coupled to the Spacer Phosphoramidite (Clonetech). Synthesis of the second oligonucleotide segment was then carried out in the opposite (5'→3') direction using 5'-phosphoramidites (Glen Research). The resulting compound consisted of two oligonucleotide segments attached through their 5' ends to opposite ends of a common hexaethylene glycol phosphodiester linker.

After synthesis, all oligonucleotides were deprotected and purified as described in Example 1.

The following oligomers were prepared by this process:

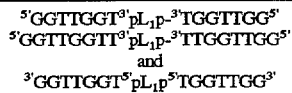

where $L_1$ represents the hexaethylene glycol chain (—CH$_2$CH$_2$—(OCH$_2$CH$_2$)$_4$—OCH$_2$CH$_2$—) linked at each end to an oligonucleotide segment by a phosphodiester linkage p, where p=—O—PO(O)—O— wherein the underlined oxygen atoms are attached directly to either end of hexaethylene glycol chain or the 5' or 3' position of the pentose moiety of the adjacent nucleotide residue.

In addition, the following uni-directional oligonucleotide containing a hexaethylene glycol derivative was prepared by standard couplings in the 3'→5' direction:

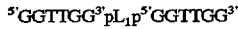

where L1 and p are as defined above.

B. Oligonucleotides joined through glycerol linkage.

In this case, the two oligonucleotide segments were both synthesized simultaneously in the standard 3'→5' direction, using the Symmetric 3'—3' Linking CPG column (1 μmole scale; CLONETECH) and standard 3'-phosphoramidites (ABI). The oligonucleotide segments were joined through their 3' ends to the glycerol linkage. The molecules were deprotected and purified as described in Example 1. The following compounds were prepared in this way:

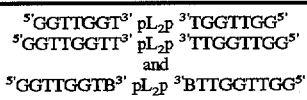

where $L_2$ represents the glycerol derivative (—CH$_2$—CH(OH)—CH$_2$—) linked at each end to an oligonucleotide segment through phosphodiester linkage p defined above in Example Two A. B represents a biotin derivative attached during solid phase synthesis by means of the Biotin ON reagent (CLONETECH).

These same techniques can be used to construct bi-directional nucleic acid ligand compounds with a phosphodiester linkage wherein the oligonucleotide segments of opposite sequence polarity are portions of nucleic acid ligands known to have affinity and specificity for certain targets such as (1) bacteriophage T4 DNA polymerase (Tuerk, C. and Gold, L., *Science* 249, 505 (1990)); (2) R17 coat protein (Schneider, D. et al., *J. Mol. Biol.* 228, 862 (1992)); (3) human immunodeficiency virus (HIV) reverse transcriptase (Tuerk, C. et al., *Proc. Nat'l. Acad. Sci. USA* 89, 6988 (1992)); (4) HIV rev protein (Barrel, D. P. et al., *Cell.* 67, 529 (1991)); (5) basic fibroblast growth factor (Jellineck, D. et al., *Proc. Nat'l. Acad. Sci. USA* 90, 11227 (1993)); (6) adenosine triphosphate (Sassanfar, M. and Szostak, J. W., *Nature* 364, 550 (1993)); and (7) theophylline (Jenison, R. D. et al., *Science* 263, 1425 (1994)). Similarly, the same techniques can be used to construct bi-directional nucleic acid ligand compounds wherein the oligonucleotide segments of opposite sequence polarity are different nucleic acid ligands that have affinity and specificity for the same target. Such nucleic acid ligands can be identified from the same or different rounds of a SELEX process.

EXAMPLE 3

Comparison of Binding Affinity for Thrombin of Known Thrombin Binding Nucleic Acid Ligand and Bi-directional Nucleic Acid Ligand Compounds Competitive binding assays were used to determine the thrombin binding affinity of the various bi-directional oligonucleotides relative to the affinity of the known thrombin aptamer 5'GGTTGGTGTGGTTGG3' (SEQ ID NO:4) (hereafter called the "consensus" aptamer; Bock, L. C. et al, *Nature* 355, 564 (1992)). The assays were performed on a BIAcore™ biosensor instrument (Pharmacia Biosensor, Uppsala Sweden) by means of Surface Plasmon Resonance (SPR) detection of thrombin bound to consensus aptamer immobilized as described in U.S. patent application Ser. No. 08/102,383, now abandoned, filed Aug. 5, 1993 incorporated herein by reference. Competition experiments were conducted at 25° C. by pre-incubating 80 nM human α thrombin for 30 minutes with various concentrations of the bi-directional oligonucleotide to be measured, in a buffer composed of 20 mM Tris-Acetate, 140 mM NaCl, 5 mM KCl, 1 mM CaCl$_2$, 1 mM MgCl$_2$ (pH 7.4). This solution was then passed over the surface containing immobilized consensus aptamer at a flow rate of 3 μL per minute for 10 minutes. The steady state response was measured as a function of bi-directional oligonucleotide concentration. The competition data were analyzed assuming that thrombin and the solution phase oligonucleotide bind monovalently and that thrombin molecules bound to a solution phase oligonucleotide are prohibited from binding to the immobilized consensus aptamer.

In this analysis, the steady state response in the presence of oligonucleotide is proportional to the surface concentration of bound thrombin, and apparent equilibrium dissociation constants ($K_d$'s) were determined from the variation in SPR response as a function of bi-directional oligonucleotide concentration. (Data were fit to eqn 31 of Pisarchick, M. L. and Thompson, N. L., *Biophys J.* 58, 1235, to yield the $K_d$ values. In this analysis, it was assumed that the concentration nucleic acid ligand free in solution is equal to the total nucleic acid ligand concentration). The values determined are shown below (SEQ ID NO:4):

| Nucleic Acid Ligand | Compound | Apparent $K_d$ |
|---|---|---|
| 5'GGTTGGTG3'-p-3'TGGTTGG5' | 1 | 224 nM |
| 5'GGTTGGTT3'-p-3'TTGGTTGG5' | 2 | 312 nM |
| 5'GGTTGGTTG3'-p-3'TTGGTTGG5' | 3 | 11 nM |
| 3'GGTTGGTT5'-p-5'TTGGTTGG3' | 4 | 25 nM |
| 5'GGTTGGT3'-$L_1$-3'TGGTTGG5' | 5 | 9 nM |
| 5'GGTTGGTT3'-$L_1$-3'TTGGTTGG5' | 6 | 10 nM |
| 3'GGTTGGT5'-$L_1$-5'TGGTTGG3' | 7 | 23 nM |
| 5'GGTTGGT3'-$L_2$-3'TGGTTGG5' | 8 | 29 nM |
| 5'GGTTGGTT3'-$L_2$-3'TTGGTTGG5' | 9 | 19 nM |
| 5'GGTTGGTGTGGTTGG3' (consensus) | 10 | 6 nM |
| 5'GGTTGG3'p$L_1$p 5'GGTTGG3' | 11 | 29 nM |
| 5'GGTTGGTT3' | 12 | 1500 nM |

EXAMPLE 4

Increased Clotting Time with Bi-directional Nucleic Acid Ligand Compounds

This example demonstrates inhibition of thrombin conversion of fibrinogen to fibrin in the presence of whole platelet-poor porcine plasma (PPP) by bi-directional nucleic acid ligand compounds of this invention.

Figure 2:
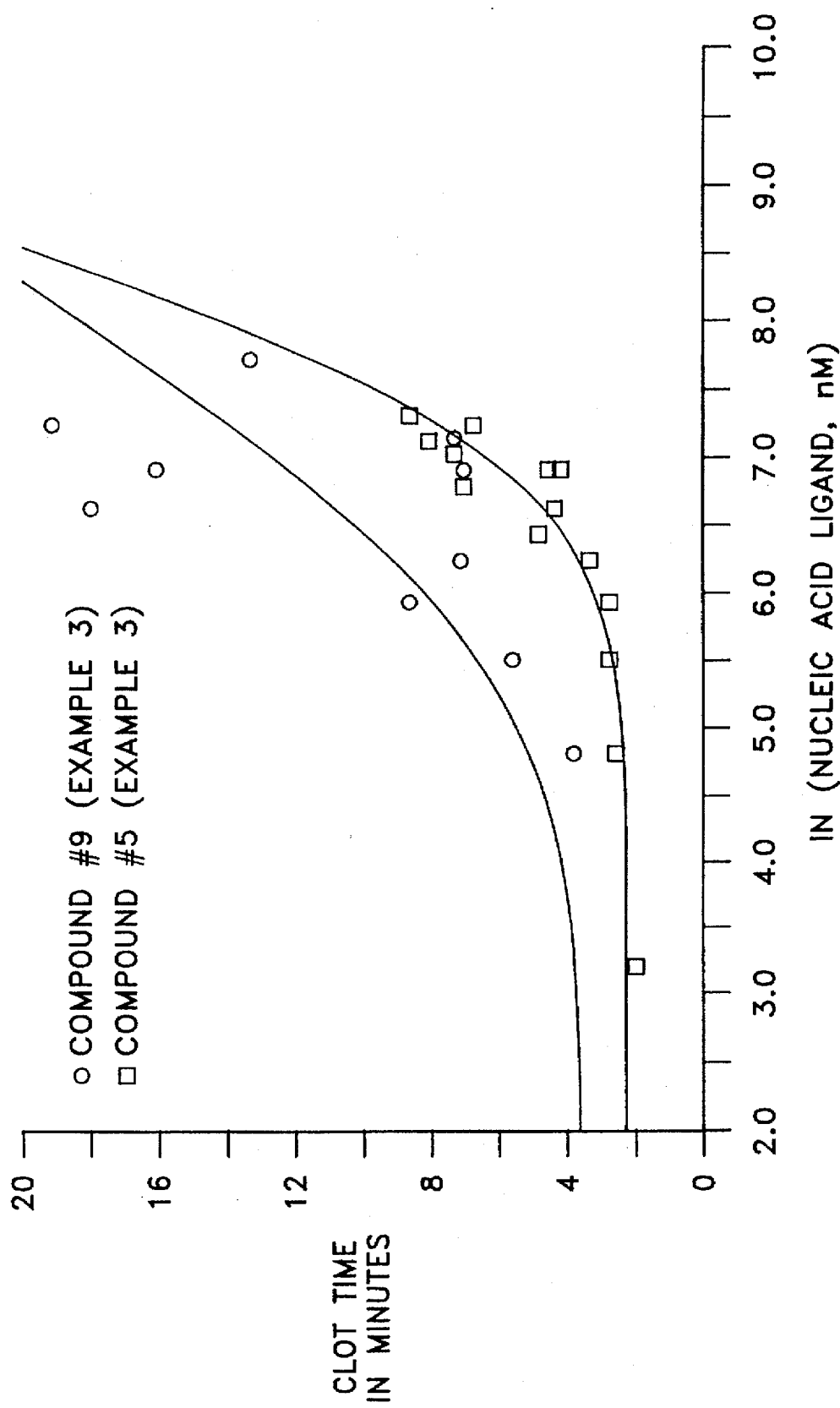
FIG. 2 is a graph which depicts the inhibition of thrombin conversion of fibrinogen to fibrin by bi-directional nucleic acid ligand compounds of the present invention.

PPP was prepared by separating cells from serum by centrifugation of whole citrated porcine blood (Environmental Diagnostics Inc.). Approximately 0.5 ml of PPP was added to 12×75 mm polystyrene test tubes (FALCON, Becton Dickinson) and equilibrated to room temperature in a water bath for 15 minutes. Following equilibration, 25 µl of 250 µg/ml bovine thrombin (Sigma) in saline was added along with varying amounts of bi-directional nucleic acid ligand compounds prepared in Example 3 (specifically Compound #5 and Compound #9) in saline and sufficient saline diluent to bring the total volume to 0.6 ml. At this time 50 µl of 0.4M $CaCl_2$ was added to initiate coagulation and the tubes were quickly capped. Tube contents were mixed on a laboratory inverting mixer and time of clotting noted for each tube type. FIG. 2 graphically summarizes results of the clot time assay by these two bi-directional nucleic acid compounds demonstrating inhibition of exogenous thrombin in plasma.

EXAMPLE 5

Bi-directional Nucleic Acid Ligand Resistance to 3' Exonuclease

This example demonstrates the ability of 3'—3' linked nucleic acid ligands (bi-directional nucleic acid ligands) to resist degradation by a commercial 3'-exonuclease derived from snake venom. It is expected that the 3'—3' linked oligonucleotides will show similar resistance to 3'-exonucleases found in The various bi-directional nucleic acid ligands to be tested were first labeled with radioactive ($^{32}$p) phosphate as follows:

200 pmol of each oligonucleotide was incubated at 37° C. for 30 minutes in 20 µl of a solution containing 3.0 mM Tricine (pH 7.6), 50 mM TRIS-HCl (pH8), 10 mM $MgCl_2$, 5 mM DTT, 1.0 µM γ-$^{32}$P-ATP (3000 Ci/mmol, 10 mCi/mL), 10 units T4 polynucleotide kinase (New England Biolabs). This labeling reaction was then terminated by heating the mixture at 95° C. for 3 minutes.

To test the resistance of the $^{32}$P-labeled oligonucleotides to the 3' exonuclease, the following reaction mixtures were assembled: Each bi-directional nucleic acid ligand (25 pmole) was dissolved in 100 µl containing 55 mM Tris-HCl, 55 mM NaCl, 7.5 mM $MgCl_2$ (all at pH8.8). To this mixture 0.005 units of the exonuclease (Phosphodiesterase I; C. adamanteus Venon; Pharmacia Biotech, Inc.) was added and the sample was mixed and incubated at 37° C. Five µL aliquots of each reaction were removed at 3, 10, 30, 60, and 100 minutes. The reactions were quenched by placing the aliquots into 25 µL solutions containing 50% (w/v) urea, 20 mM $Na_2EDTA$, and 0.05% bromophenol blue/zylene cylanol and heating the sample to 90° C. for 2 minutes. The reaction products were analyzed by electrophoretic separation on a denaturing polyacrylamide gel and subsequent autoradiagraphy of the gel.

The half-lives of the various bi-directional nucleic acid ligands under these conditions were estimated by visual inspection of autoradiogram (SEQ ID NO:4):

| Nucleic Acid Ligand | Approximate Half-Life |
|---|---|
| 5'GGTTGGTTG3'-p-3'TTGGTTGG5' | >100 minutes |
| 5'GGTTGGT3'-$L_1$-3'TGGTTGG5' | 30 minutes |
| 5'GGTTGGTT3'-$L_2$-3'TTGGTTGG5' | >100 minutes |
| 5'GGTTGGTGTGGTTGG3' (consensus) | <3 minutes |

The nucleic acid ligonds that, by virtue of their bi-directionality, lack 3'-terminal nucleoside residues show considerable resistance to degradation by the 3'-exonuclease, exhibiting half-lives of 30 minutes or longer under the reaction conditions studied. In contrast, the consensus ligand, which does contain a 3'-terminal nucleoside, is completely degraded by the enzyme in less than 3 minutes under these conditions.

The foregoing is illustrative of the present invention, and is not intended to be construed as limiting thereof. As numerous alternatives to those methods and compounds described above which incorporate the present invention will be apparent to those skilled in the art, the invention is accordingly defined by the following claims.

---

---

What is claimed is:

1. A bi-directional nucleic acid ligand compound comprising at least two oligodeoxyribonucleotides each independently selected from the group consisting of SEQ ID NO: 1, SEQ ID NO:2 and SEQ ID NO:3, wherein the two oligodeoxyribonucleotides are linked either directly or by a connecting compound in a 5' to 5' or a 3' to 3' orientation.

2. The bi-directional nucleic acid ligand compound of claim 1 wherein the at least two oligodeoxyribonucleotides are linked to the connecting compound at their respective 3' terminii.

3. The bi-directional nucleic acid ligand compound of claim 2 wherein the connecting compound is a phosphodiester compound.

4. The bi-directional nucleic acid ligand compound of claim 3 wherein the phosphodiester compound is hexaethylene glycol phosphodiester.

5. The bi-directional nucleic acid ligand compound of claim 3 wherein the phosphodiester compound is glycerol phosphodiester.

6. The bi-directional nucleic acid ligand compound of claim 3 wherein the phosphodiester compound is a phosphodiester linkage.

7. The bi-directional nucleic acid ligand compound of claim 2 having two oligodeoxyribonucleotides, and wherein the two oligodeoxyribonucleotides comprise SEQ ID NO: 1.

8. The bi-directional nucleic acid ligand compound of claim 7 wherein the two oligodeoxyribonucleotides are linked at their respective 3' terminii by a hexaethylene glycol phosphodiester linkage.

9. The bi-directional nucleic acid ligand compound of claim 2 having two oligodeoxyribonucleotides, and wherein the two oligodeoxyribonucleotides comprise SEQ ID NO:2.

10. The bi-directional nucleic acid ligand compound of claim 9 wherein the two oligodeoxyribonucleotides are linked at their respective 3' terminii by a hexaethylene glycol phosphodiester linkage.

11. The bi-directional nucleic acid ligand compound of claim 2 having two oligodeoxyribonucleotides, and wherein one of the two oligodeoxyribonucleotides comprises SEQ ID NO:2 and the other oligodeoxyribonucleotide comprises SEQ ID NO:3.

12. The nucleic acid ligand compound of claim 11 wherein the two oligodeoxyribonucleotides are linked at their respective 3' terminii by a phosphodiester linkage.

13. The bi-directional nucleic acid ligand compound of claim 1 wherein the at least two oligodeoxyribonucleotides are linked to the connecting compound at their respective 5' terminii.

14. The bi-directional nucleic acid ligand compound of claim 13 wherein the connecting compound is a phosphodiester compound.

15. The bi-directional nucleic acid ligand compound of claim 14 wherein the phosphodiester compound is hexaethylene glycol phosphodiester.

16. The bi-directional nucleic acid ligand compound of claim 14 wherein the phosphodiester compound is glycerol phosphodiester.

17. The bi-directional nucleic acid ligand compound of claim 14 wherein the phosphodiester compound is a phosphodiester linkage.

* * * * *